United States Patent [19]

Friedrich et al.

[11] 4,436,697
[45] Mar. 13, 1984

[54] SOLDERING ALLOY

[75] Inventors: Ronald Friedrich, Kamp-Lintfort; Manfred Müller, Essen, both of Fed. Rep. of Germany

[73] Assignee: Fried. Krupp Gesellschaft mit beschränkter Haftung, Essen, Fed. Rep. of Germany

[21] Appl. No.: 422,193

[22] Filed: Sep. 23, 1982

[30] Foreign Application Priority Data

Nov. 20, 1981 [DE] Fed. Rep. of Germany ....... 3145944

[51] Int. Cl.³ ...................... C22C 19/07; C22C 30/00
[52] U.S. Cl. .................................. 420/440; 420/583; 420/588
[58] Field of Search ............... 420/440, 583, 588, 436; 148/425, 442; 228/263 B, 263.13

[56] References Cited

U.S. PATENT DOCUMENTS 2,213,207  9/1940  de Golyer ........................ 420/436
2,553,609  5/1951  Schmidt ........................... 420/583

Primary Examiner—Peter K. Skiff
Attorney, Agent, or Firm—Spencer & Frank

[57] ABSTRACT

A soldering alloy containing 25 to 35% iron, 15 to 25% chromium, 3 to 6% silicon, 1 to 4% molybdenum, the remainder essentially cobalt.

4 Claims, No Drawings

SOLDERING ALLOY

BACKGROUND OF THE INVENTION

The present invention relates to a soldering alloy, and more particualrly to a soldering alloy which can be used specifically in the dental art.

According to the prior art, gold alloys or nickel alloys are used in the dental art to hard solder prosthesis frames. It is known that alloys containing nickel may cause allergic reactions when they come in contact with the skin. Moreover, it is known that vapors and dusts from nickel alloys can cause carcinogenic reactions in the lungs of human beings so that the processing of such nickel alloys involves health endangering risks. This applies especially for the use of nickel alloys in the dental field, e.g. in the production of dental prostheses and/or implants.

SUMMARY OF THE INVENTION

It is an object of the present invention to provide a solder or a soldering alloy which does not have the above-mentioned disadvantages and which possesses, especially in the dental art, the wettability, mechanical stressability and adhesive strength required for binding together the soldered parts.

Additional objects and advantages of the present invention will be set forth in part in the description which follows and in part will be obvious from the description or can be learned by practice of the invention. The objects and advantages are achieved by means of the processes, instrumentalities and combinations particularly pointed out in the appended claims.

To achieve the foregoing objects, and in accordance with its purpose, the present invention provides a soldering alloy comprising 25 to 35% iron, 15 to 25% chromium, 3 to 6% silicon, 1 to 4% molybdenum, the remainder essentially cobalt.

Advantageously, this soldering alloy also contains 0.1 to 1% manganese, 0.5 to 2% vanadium and 0.1 to 1% boron.

It is to be understood that both the foregoing general description and the following detailed description are exemplary, but are not restrictive of the invention.

DETAILED DESCRIPTION OF THE INVENTION

The soldering alloy of the present invention contains iron, chromium, silicon, molybdenum and cobalt as essential elements. The soldering alloy generally contains, based on the weight of the alloy, 25 to 35% iron, 15 to 25% chromium, 3 to 6% silicon, 1 to 4% molybdenum, and the remainder essentially cobalt. By remainder essentially cobalt, it is understood that the soldering alloy can contain additions of other ingredients. Advantageously, the soldering alloy contains, on a weight basis, 0.1 to 1% manganese, 0.5 to 2% vanadium and 0.1 to 1% boron as additional ingredients. Preferably, the soldering alloy consists essentially of the above essential elements, with or without the above additions of manganese, vanadium and boron.

The soldering alloy of the present invention having the above composition possesses excellent flow properties and it has been proven to be tolerated by tissue. In addition, no special protective measures are required during the processing of this soldering alloy since it is free of nickel. Finally, the alloy according to the present invention shows excellent binding properties during the soldering of Co-Cr alloys as frequently used in the medical art.

In a specific embodiment of the present invention, a soldering alloy was prepared which contained 5.3% silicon, 0.4% manganese, 21.7% chromium, 2.7% molybdenum, 1.05% vanadium, 0.5% boron, 29% iron, with the remainder cobalt. This soldering alloy was used to solder together parts of tooth prostheses made of a cobalt-chromium alloy.

The soldering connection is extremely durable and has excellent mechanical properties, and above all high resistance to corrosion. Working with the solder was easy since it flows well.

It will be understood that the above description of the present invention is susceptible to various modifications, changes and adaptations, and the same are intended to be comprehended with the meaning and range of equivalents of the appended claims.

What is claimed is:

1. Soldering alloy comprising 25 to 35% iron, 15 to 25% chromium, 3 to 6% silicon, 1 to 4% molybdenum, and the remainder essentially cobalt.

2. Soldering alloy according to claim 1, which contains 0.1 to 1% manganese, 0.5 to 2% vanadium, and 0.1 to 1% boron.

3. Soldering alloy consisting of 25 to 35% iron, 15 to 25% chromium, 3 to 6% silicon, 1 to 4% molybdenum, and remainder cobalt.

4. Soldering alloy consisting of 25 to 35% iron, 15 to 25% chromium, 3 to 6% silicon, 1 to 4% molybdenum, 0.1 to 1% manganese, 0.5 to 2% vanadium, 0.1 to 1% boron and remainder cobalt.

* * * * *